United States Patent
Kirk, III et al.

(10) Patent No.: US 8,794,858 B2
(45) Date of Patent: Aug. 5, 2014

(54) DISPENSER HANDLE

(75) Inventors: Karl Dallas Kirk, III, New York, NY (US); Paul J. Mulhauser, New York, NY (US)

(73) Assignee: OptMed Inc., Woodmere, NY (US)

( * ) Notice: Subject to any disclaimer, the term of this patent is extended or adjusted under 35 U.S.C. 154(b) by 0 days.

(21) Appl. No.: 13/488,384

(22) Filed: Jun. 4, 2012

(65) Prior Publication Data

US 2013/0004229 A1 Jan. 3, 2013

Related U.S. Application Data (60) Provisional application No. 61/493,425, filed on Jun. 4, 2011.

(51) Int. Cl.
*B65D 35/28* (2006.01)
*B65D 37/00* (2006.01)
*B05B 11/04* (2006.01)
*A61M 35/00* (2006.01)
*A45D 34/04* (2006.01)

(52) U.S. Cl.
CPC ............ *B05B 11/048* (2013.01); *A61M 35/003* (2013.01); *A45D 34/04* (2013.01)
USPC ............ 401/135; 401/132; 401/133; 222/95; 222/214; 222/103

(58) Field of Classification Search
USPC ......... 401/132, 133, 134, 135, 145, 152, 158; 222/95, 214, 103; 604/3
See application file for complete search history.

(56) References Cited

U.S. PATENT DOCUMENTS

| | | | |
|---|---|---|---|
| 6,315,165 B1 * | 11/2001 | Regan | 222/103 |
| 6,536,975 B1 | 3/2003 | Tufts | |
| 6,669,055 B1 * | 12/2003 | Coleman et al. | 222/103 |
| 8,342,765 B2 * | 1/2013 | Stenton | 401/186 |
| 2004/0254561 A1 * | 12/2004 | Stenton | 604/500 |
| 2008/0046004 A1 * | 2/2008 | Stenton | 606/214 |
| 2008/0167681 A1 * | 7/2008 | Stenton | 606/214 |
| 2009/0311030 A1 * | 12/2009 | Stenton | 401/165 |

* cited by examiner

*Primary Examiner* — David Walczak
*Assistant Examiner* — Joshua Wiljanen
(74) *Attorney, Agent, or Firm* — Edward K. Welch, II; IP&L Solutions (57) ABSTRACT

A hand-held dispenser handle for use with tubular containers, especially unit dose or single use containers, of various liquids or viscous fluids, which provides enhanced flow and locus control.

20 Claims, 5 Drawing Sheets

FIG. 11C   FIG. 11B ant Application No. 61/493,425, filed on Jun. 4, 2011, the content of which is hereby incorporated herein by reference in its entirety.

The present invention is directed to an improved dispenser handle for use with resilient tubular containers of a liquid or flowable material.

BACKGROUND

Many liquids and viscous fluids are packaged in compressible tubular containers comprising a tubular container body having a closed end and a dispensing outlet at an open end whereby dispensing is effect by compressing the wall of the container body. However, it is very difficult to control the flow of material from the dispensing outlet owing to a number of factors including the viscosity of the fluid; the presence of flow restriction elements, such as filters, porous tips, and the like; and the general difficulty of an individual in initiating a proper and consistent pressure on the exterior of the container body to provide a consistent and suitable flow while avoiding the application of too much pressure whereby fluid is prematurely and/or excessively dispensed. It is especially difficult to maintain a proper pressure for the full duration of the desired flow. In addition, difficulty arises because these compressible tubular containers, particularly for unit dose or one-time applications, are short in length and are held and pressed between the thumb and forefinger, whereby precision dispensing is wholly contingent upon the individual firmly holding the compressible tubular container between the fingers while compressing the container body.

These problems are magnified where the liquid or viscous fluid, or a component thereof, is contained within a crushable ampoule within the lumen of the tubular container. Here one must apply sufficient pressure to crush the ampoule, thereby overcoming the inherent resistance and strength properties of the ampoule wall, while avoiding too much pressure which will cause an eruption of the liquid or viscous fluid from the dispensing outlet concurrent with the crushing of the ampoule wall. These devices have yet another key concern as the ampoules are most often made of glass or another rigid, breakable material, especially a plastic material. Owing to the thin nature of the compressible container wall, it is not uncommon for the glass or plastic shards to penetrate the compressible tubular container wall, cutting into the fingers of the individual using the same. These piercings also provide opportunities for the liquid to leak out of the container.

Many developments have been made to address many of these problems, several of which have addressed multiple problems at the same time. For example, Regan (U.S. Pat. No. 6,315,165 B1), although not employing an ampoule, nonetheless provides better dispensing control through the use of a device having opposing jaw elements which have a flat surface which lies against and presses against the side walls of a crimped tube to force material out of the tube opening. While an improvement, since the pressure is uniform across the tube surface, this configuration still has flow control issues.

Similarly, many improvements have been made to those devices which employ an ampoule. For example, D'Alessio et. al. (U.S. Pat. No. 6,478,191 B1) teach the use of a barrier which covers the exterior portion of the tubular container corresponding to the point or area of compression. The barrier is typically a polymer film which is wrapped about the circumference of the tubular container. Alternatively, D'Alessio et. al. (US 2003/0080151 A1) and Morane et. al. (U.S. Pat. No. 3,964,643) teach the use of similar barrier materials which are wrapped around the exterior circumference of the ampoule, all of which lies within the lumber of the compressible tubular container. While effective, these developments only address the problem with shards cutting the user and/or allowing for leakage through the pierced tubular container walls. In the meantime, it adds costs of materials and manufacturing complexity. Furthermore, because is it part of the container, it too is disposed of once the materials are dispensed: thereby adding more waste into the waste stream.

Koreska et. al. (U.S. Pat. No. 4,784,506), on the other hand, provides for a reusable device whose reusable body incorporates a pair of opposing blades each having a tappet facing inward and offset to one another, whereby pressure applied to the blades causes the tappets to break the ampoule within the body of the device. However, once the ampoule is broken, dispensing is reliant upon the natural flow of the liquid and the absorptive properties of the absorbent tip. The device of Koreska et. al. does not need nor does it have any means for increasing pressure within the casing holding the ampoule to facilitate dispensing of the liquid. Rather, it merely requires the tappets to break the ampoule.

While the art has endeavored to address and has to a limited extent achieved success in addressing many of these issues; others still exist.

Accordingly, there remains a need for a device having an improved gripping structure which allows for a more controlled, manual dispensing of a liquid or viscous fluid material from a container associated with that device. In following, there remains a need for such a device which also and simultaneously provides for greater and controlled accuracy in the locus of the dispensing of the material.

Additionally, there remains a need for a device for use with containers of liquid or viscous fluid composition, especially those packaged as a unit dose, wherein the liquid or viscous fluid composition, or a component thereof, is contained within a crushable ampoule within the main container body, which device allows for the manual and controlled crushing of the ampoule without inadvertent dispensing of the contents and/or, as desired, the concurrent and controlled dispensing of the contents. Furthermore, there remains a need for such a device which avoids concerns with shards of the crushed ampoule piercing the container wall and injuring the user.

Furthermore, there remains a need for a dispenser handle for use with tubular containers, especially unit dose containers, which are simple and inexpensive to construct relative to prior art applicators and which are reusable.

SUMMARY OF THE INVENTION

Accordingly, in one of its aspects, the present invention provides an improved hand-held dispenser handle having a body for holding a container of the material to be dispensed and associated therewith or integrated therein a tongs structure which may be squeezed to dispense the material within the container. The combination of the dispenser handle body and tongs provide a more ergonomically suitable dispenser handle allowing for more controlled and steady dispensing.

In another of its aspects, the present invention provides a hand held dispenser handle for use with a container having an ampoule within its body, which ampoule contains or contains a part of the composition to be dispensed. The dispenser handle has tongs associated therewith comprising a pair of opposing arms which arms, when pressed towards one another, effect the crushing of the ampoule and, in following, the dispenser of the material within the ampoule. This construction prevents or lessens any concern for injury to the user from shards created upon crushing the ampoule.

In yet another of its aspects, the present invention provides for a reusable dispenser handle which permits single-handed operation with improved control in terms of both dispensing rate and dispensing locus.

In a still further aspect, the present invention provides for a one-piece reusable dispenser handle which is simple to manufacture and therefore may be manufactured more economically than prior art applicators.

In accordance with these and other aspects evident from the following description, the dispenser handle is adapted to receive a primary container of a liquid or viscous fluid composition which primary container may be dual chambered, a dual chambered container either having two compartments separated by a crushable wall or a crushable ampoule residing within the lumen of the primary container. In the case of the dual chambered containers, the dispenser handle is configured to crush the dividing wall or ampoule without crushing or causing a breach of the primary container outer wall. As noted, the dispenser handle comprises as its two primary elements a body and a tongs or tongs-like structure associated with and attached to or integrated into the midsection of the body. The body has a distal end which is elongated so as to sit in the crux of ones hand between the thumb and forefinger, i.e., on the webbing of the thenar space, much like most people hold a pencil, and a proximal end which is defined by a barrel for receiving the container of the liquid or viscous fluid to be dispensed. The arms of the tongs or tongs-like structure are spaced from one another and are directed towards the proximal end of the body so that when the user holds the dispenser handle, the thumb and forefinger are each on an opposing arm of the tongs structure and the distal end of the body lies on the webbing of the thenar space. The inner or opposing surfaces of the arms have contoured superstructures associated therewith for making contact with the outer surface of the primary container for exerting a controlled pressure on the container wall which flexes under the pressure to thereby create pressure within the container and dispense the material in the container. The superstructure preferably includes a distinct protrusion or tappet element at a point past the end of the proximal end of the body such that the tappet causes the crushing of the dividing wall or ampoule when the arms are moved towards one another.

Various iterations of the dispenser handle body are contemplated. For example, the body may be hollow or, but for the barrel, may be solid: though for economic reasons a hollow body is preferred. The hollow body will preferably have a plurality of spaced, longitudinal ribs protruding from its inner surface which ribs extend from the distal end of the body to the bottom of the barrel in the proximal end of the body. Each rib extends into the interior of the body to a sufficient extent that the butt ends of the ribs define the bottom of the barrel and/or serve as a stop element: in either case defining the maximum depth to which the container can be inserted into the barrel. Preferably, for purposes of cost of materials and molds, the body will have two opposing ribs both of which are preferably situated in a plane which also includes the longitudinal axis of arms of the tongs. In this manner, the ribs provide extra strength to the body at the point of integration of the tongs into the body.

As evident from the foregoing, the barrel serves as the seat for the container to be inserted into the dispenser handle. The barrel comprises the proximal end of the container body and will have dimensions that are typically characterized as squared or, preferably, over squared, i.e., the former indicating the width and depth are the same, the latter that the depth is greater than the width. The barrel may have a smooth inner wall or a ribbed inner wall. In the former, the diameter of the barrel is typically the same as or substantially the same as the diameter of the container to be inserted therein, but is preferably slightly smaller than that of the container so as to provide a slight interference fit: thereby securing the container in the barrel. In the latter, the barrel may have a diameter that is somewhat, preferably only slightly, larger than the diameter of the container to be inserted therein, with an inner wall having a plurality of spaced, preferably evenly spaced, longitudinal ribs. The ribs extend into the volume of the barrel to a sufficient extent to create a slight interference fit between the peak of the ribs and the outer wall of the container upon insertion of the container into the barrel.

Similarly, various iterations are contemplated for the superstructures on the inner surfaces of the arms of the tongs which superstructures are responsible for directly impacting upon the container outer wall. For example, the inner surfaces of the arms may have press plates extending away from the inner surfaces towards one another, which press plates engage and squeeze the container as the arms are moved towards one another. The press plate may be in the form of a press panel which is a planar surface extending along the longitudinal axis of the arm and perpendicular to the plane of the arm, which press panel ends in a curved edge which acts upon the outer wall of the container. Alternatively, the press plate may be a curved band extending away from the inner surface of the arm but whose proximal and distal ends connect with the arm at points towards the proximal and distal ends of the arm and whose transverse axis is parallel to the transverse axis of the arm. Alternatively, and preferably, the superstructure has both the press panel and the curved band wherein the press panel is contiguous with the inner wall of the arm and with the opposing face of the band, thereby providing reinforcement to the band. Finally, the band may have an area, generally the same area that serves as the tappet, having a contoured surface wherein the contour mimics the contour of the container to be placed in the barrel so that there is an extended surface area contact between the press band and the outer wall of the container upon initial contact of the same with each other.

In accordance with another embodiment, the arms of the tongs structure may be connected by a collar element which resides midway between the two arms and is situated away from and in front of the proximal end of the dispenser handle body with the central axis through the collar and the longitudinal axis of the barrel being one and the same. In this embodiment, the lumen of the collar preferably has the same diameter as container to be inserted there through or it may have a slight interference fit with the container wall so that the collar helps hold and secure the container in the dispenser handle. The collar generally connects and resides between the two tappet regions of each arm and, thus, becomes the initial point of pressure on the container wall for initiating and promoting pressurized dispensing. In dual chambered containers, the collar also serves as the tappet or crushing mechanism for crushing the dividing wall or ampoule.

In use, the arms of the tongs structure are squeezed toward one another causing press plates to contact the outer wall of the container and exert pressure thereon. Continued exertion will lead to the dispensing of the liquid or viscous fluid from the container outlet. In the case of those containers having a dual chamber, the arms of the tongs are initially pressed to a sufficient extent to crush the dividing wall or ampoule, as appropriate. The pressure is then typically released or backed off to an extent, to prevent an eruption of fluid from the orifice. Thereafter, the application of pressure, though typically less, is resumed to initiate flow.

The present invention further provides a method of applying a liquid or viscous fluid from a container using a dispenser handle which is adapted to hold said container, the method comprising the steps of (a) providing a dispenser handle comprising a body having distal and proximal ends and a tongs or tongs-like structure associated with and attached to or integrated into the midsection of the body, wherein the distal end of the body is elongated and the tongs structure has a pair of spaced opposing arms extending from the midsection of the body to and past the proximal end of the body, wherein the inner surfaces of the arms have associated therewith or integrated therein a press plate superstructure which extends from the inner surface of the arms towards one another and are contoured to allow for a point or area contact with a container body which lies in and extends from a barrel in the proximal end of the handle body, whereby movement of the arms towards one another causes the press plate to engage and exert pressure on outer wall of the container to thereby initiate dispensing of the contents of the container, (b) inserting the closed end of a tubular container into the open end of the barrel in the proximal end of the handle body and (c) squeezing the arms towards one another so as to dispense the contents from the container. The present invention also applies to a method of applying a liquid or viscous fluid composition wherein the material to be dispensed or a component thereof is contained in a second chamber in the container which is separated by a dividing wall or which comprises an ampoule within the lumen of the container and the dispenser handle includes tappet elements which, upon pressing of the arms causes the dividing wall or ampoule to fracture.

Additional aspects of the invention, together with the advantages and novel features appurtenant thereto, will be set forth in part in the description which follows, and in part will become apparent to those skilled in the art upon examination of the following and the attached drawings, or may be learned from the practice of the invention. The objects and advantages of the invention may be realized and attained by means, instrumentalities and combinations particularly pointed out in the appended claims.

BRIEF DESCRIPTION OF THE DRAWINGS

The accompanying drawings which form a part of the specification are to be read in conjunction therewith. Like reference numerals are employed to indicate like parts in the various views.

DETAILED DESCRIPTION OF THE PREFERRED EMBODIMENT

In the following description, unless otherwise stated, it is to be understood that the dispenser handle body and barrel are cylindrical in shape and share the same longitudinal or cylinder axis. However, it is also to be understood that dispenser handle bodies and barrels of different cross-sectional shape, such as elliptical, ovoid, rectangular, square, hexagonal, etc., are also within the teachings of this specification. Further, it is to be noted that for ease of understanding, the orientation and features of the dispenser handle as well as the components or features thereof are referenced in terms of distal and proximal ends or regions as well as their orientation relative to the longitudinal axis of the dispenser handle body. The proximal end of the dispenser handle body is that end associated with the barrel and into which the container is inserted upon use and the distal end is the opposite end of the handle body. In following, the distal end of an element or feature of the dispenser handle is generally that end which is closest to the distal end of the handle body and the proximal end is the opposite end of the stated element or feature.

Figure 11:
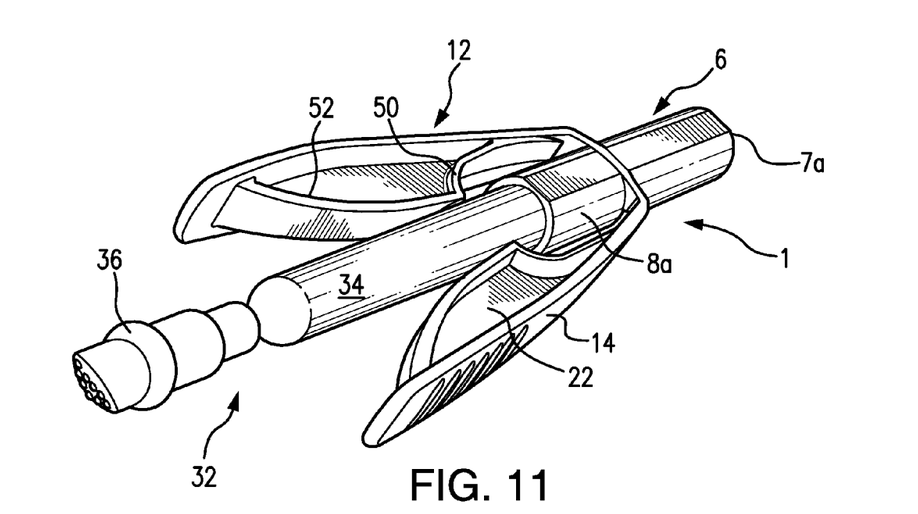
FIG. 11 is an elevated perspective view of an assembled liquid dispenser employing the dispenser handle of FIG. 1.
Figure 11A:
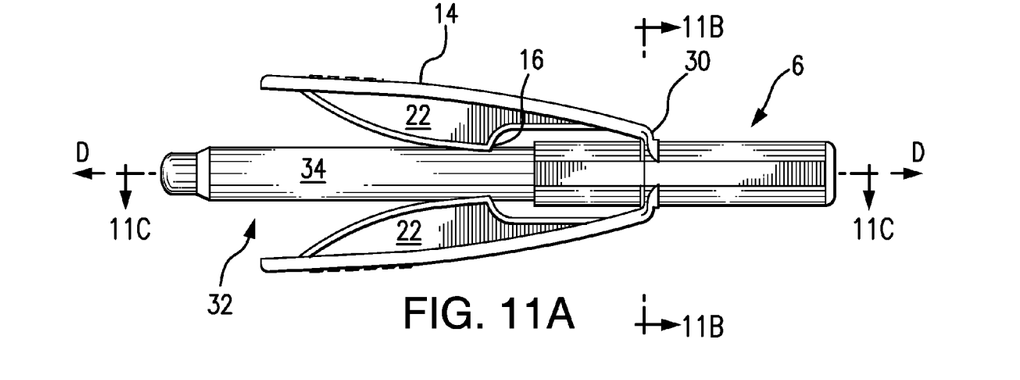
FIG. 11A is top plan view of the dispenser assembly of FIG. 11.
Figure 11B:
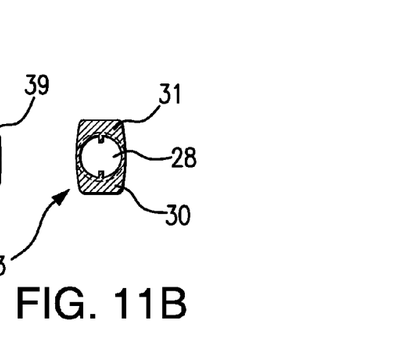
FIG. 11B is a cross-sectional view taken generally along the line 11B-11B of FIG. 11A.

Referring to the drawings in general and initially to FIGS. 1, 1A, 1B, 11 and 11A in particular, where like reference numerals identify like elements in the various views, a dispenser handle manifesting aspects of the invention is illustrated and designated generally by the numeral 1. The dispenser handle 1 generally includes a generally tubular body 6 having a distal region 7 ending at a distal end 7a and a proximal region 8 ending at a proximal end 8a wherein the proximal region defines a barrel 10 having an open end 11 coinciding with the proximal end 8a which is adapted to receive a container 32 containing a liquid or viscous fluid to be dispensed. Associated about the midsection of the body is a tongs or tongs-like structure 12 having a pair of diametrically opposed arms 14 angled away from the body and extending past the proximal end 8 of the body in a spaced relationship. The arms may be directly connected to the dispenser body, but, as shown more clearly in FIGS. 1A and 11A, preferably extend from hinge elements 30 which extend perpendicularly from the longitudinal axis D of the dispenser body (shown by the arrows in FIG. 11A). FIG. 11B is a cross-sectional view of the body at the point where the hinge elements 30 extend from the body wherein the dashed circular line 31 of FIG. 11B shows the cylindrical outline of the body at the point of integration of the tongs.

Figure 1:
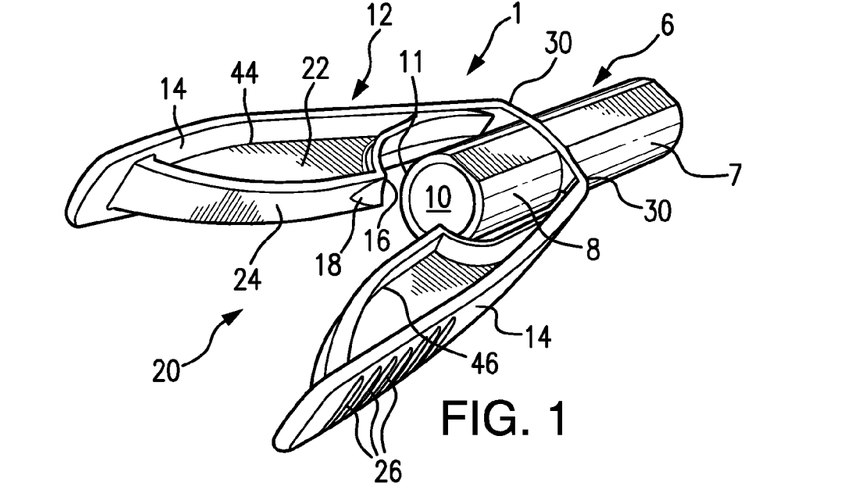
FIG. 1 is an elevated perspective view of a dispenser handle constructed in accordance with a preferred embodiment of the present invention.
Figure 1A:
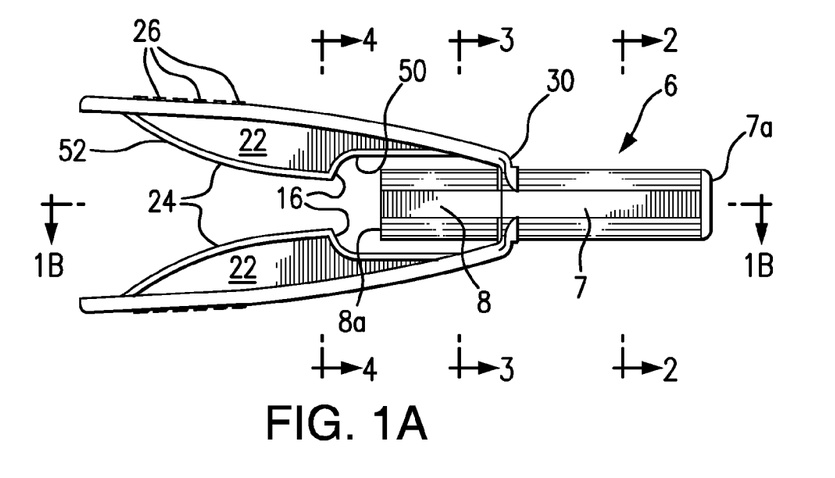
FIG. 1A it a top plan view of the dispenser handle of FIG. 1.

As seen in FIGS. 1 and 1A, the body 6 of the dispenser handle 1 is an elongated tubular element having, as noted, a distal portion 7, which is typically hollow with a plurality of spaced ribs, and a proximal portion 8 having a cylindrical hollow or barrel 10 at the proximal end 8a. The depth of the barrel 10 is that which is sufficient to securely hold the closed end of a container of a liquid or viscous fluid to be dispensed in the dispenser handle body whereby the container as a whole is secured in the dispenser handle. Generally, the barrel is squared, the depth is the same as the diameter, but is preferably over squared, whereby the depth is greater than the diameter. At the same time, one does not want the depth too large as that may interfere with the overall operation of the container in the dispenser handle, especially if the tappet region of the arms first engages the container body at or past its midpoint. Typically, the depth will be no more than three times, preferably no more than twice the diameter of the container body to be inserted into the barrel. Typically, the thickness of the barrel wall 15 is between about 0.8 mm and about 2 mm, preferably from about 0.8 mm and about 1.5 mm. In this regard, especially if the hinge, as described below, is attached below the barrel, the barrel wall has no need for too much rigidity or integrity as its purpose is only to securely hold the end of the container. Typically the body will be from about 4 cm to about 8 cm, preferably from about 5 cm to about 7 cm, in length.

Figure 1B:
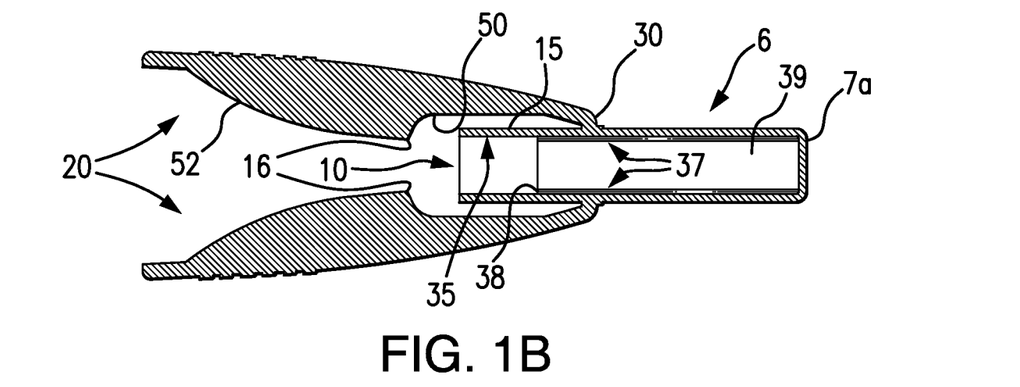
FIG. 1B is a cross-sectional view of the dispenser handle of FIG. 1A taken generally along the line 1B-1B.
Figure 2:
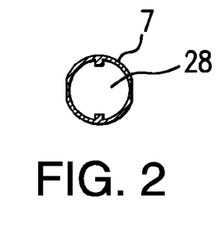
FIG. 2 is a cross-sectional view taken generally along line 2-2 of FIG. 1A.
Figure 3:
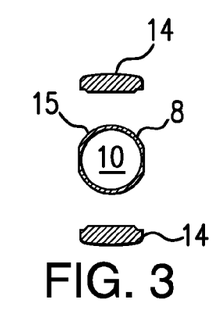
FIG. 3 is a cross-sectional view taken generally along line 3-3 of FIG. 1A.
Figure 4:
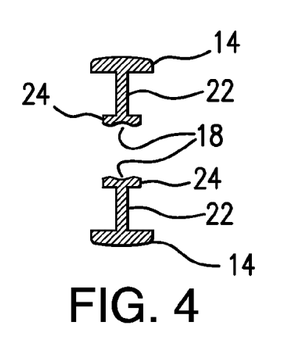
FIG. 4 is a cross-sectional view taken generally along line 4-4 of FIG. 1A.

As noted, the dispenser handle body is preferably hollow as shown in FIG. 1B, but could be solid or nearly so, below the barrel. Should the distal portion of the dispenser handle body be solid, then it is preferable that the body has a passageway either longitudinally or transversely to allow for air to flow out of and into the barrel as a container is inserted and removed, respectively, from the barrel. Preferably, the barrel is hollow with either an open or closed end, though if closed, the body preferably has a bore through the wall or the end or the barrel has ribs associated therewith, all for allowing for the release of pressure and prevention of a vacuum upon insertion and removal of a container from the barrel. More importantly, the hollow body has associated therewith a plurality of spaced, preferably evenly spaced, longitudinal ribs 37 extending from the distal end 7a to the bottom of the barrel and protruding from inner wall 35 into the interior volume 39 of the body. With this configuration, the ribs 37, or more appropriately, the butt ends 38 of the ribs define the bottom of the barrel and serve as the stop element so that the container cannot be inserted into the body further than the butt ends 38 of the ribs. Of course, in those embodiments where the barrel also has ribs, the ribs 37 in the hollow of the body may extend longitudinally to the proximal end 8a of the body, however, the height or peak of the ribs in the barrel will be considerably shorter than in the volume 39 of the body. The point at which the higher peaks transition to the lower peaks defines the bottom of the barrel whereby the transition, which is essentially a right angle at the point of transition, looks like a step whereby the step forms the barrel seat. In this regard, the step is similar to the butt ends 38 in FIG. 1B.

Figure 11C:
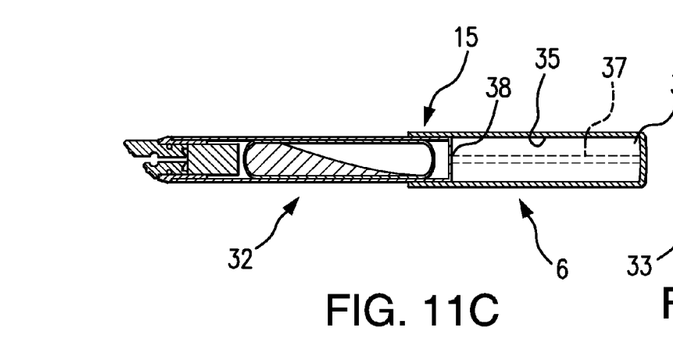
FIG. 11C is a cross-sectional view taken generally along line 11C-11C of the dispenser body and container of FIG. 11A rotated 90°.

As indicated in FIGS. 11B and 11C, at least two of the ribs 37, or both ribs in the case of a dispenser having only two ribs, are positioned on the interior wall of the body so as to lie in essentially the same plane as the longitudinal axis of the arms (which is also the plane of the press panels of the arm superstructures, if present) of the tongs. This is especially evident from FIG. 1B which shows the cross-section taken along that same plane. This positioning provides enhanced strength along the longitudinal wall of the dispenser handle body, especially in that region where the tongs are integrated into or merge with the dispenser handle body. This allows for thin walls in the dispenser handle body and, thus, additional costs savings in materials. Generally, the thickness of the wall of the hollow body will from about 1 mm to about 3 mm.

In the embodiment shown in FIGS. 1, 1B, 3 and 11, the barrel 10 is smooth walled and has an inner diameter configured to provide a slight interference fit with the outer diameter of the container 32. This prevents the container from being dislodged from the dispenser handle during use. Although not a concern with the use of a hollow body 6, where the distal portion of the body is solid, there is a concern with air being trapped between the container and the bottom of the barrel as it is being inserted, as well as a vacuum as the container is being removed. In this regard, it is preferably that the body has a passageway, either longitudinally or transversely, through the body wall and into the volume of the barrel, preferably into or at the barrel bottom, to allow for the release of pressure and prevention of a vacuum.

As shown in FIGS. 1, 1A, 3, and 4, the second key element of the dispenser handle is the tongs or tongs-like structure 12. The tongs are associated or integrated into the body at its proximal end or about its midsection, most preferably the latter, and are positioned substantially in a plane defined by the longitudinal axis of each arm of the tongs and the longitudinal axis D of the body 12 (FIG. 11A). Generally, the point of integration is at or distal to the barrel bottom 38 (FIG. 1B). While the point of integration may be forward of the barrel bottom, it is preferably that it be distal to the barrel bottom. This ensures greater structural integrity at the point of integration, especially in light of the presence of the reinforcing ribs 37. Typically, the tongs are not located more than one half, more likely no more than one third of the distance from the proximal end of the body to the distal end as measured along the longitudinal axis.

The arms 14 of the tongs 12 of the dispenser handle 1 flex about the hinges 30, the flex movement being towards and away from the longitudinal axis of the body 6. The length of the arms is sufficient to be conveniently held in the hand of the user with the distal portion of the body lying in the webbing of the thenar space. Generally, the length of the arms is similar to if not a bit longer than the length of the body. Typically, the arms will be from about 3 cm to about 8 cm, preferably from about 4 cm to about 7 cm in length. The arms are angled relative to the longitudinal axis of the body: the angle generally being determined by a line from the point of contact of the arm with the body and the touch pad. Typically the angle is from about 15° to about 35°, preferably from about 20° to about 30°, though this is somewhat dependent upon the width of the hinge flange 33 (FIG. 11B) and how far the distal ends of the arms are removed from the body, as more clearly described below. Additionally, the arms may themselves have a slight convex curvature to them so that the touch pad region of the arms, as defined below, are substantially parallel with or only angled up to about 10° from the longitudinal axis of the body. As note above, the opposing arms are spaced from one another. Generally, the distance between the proximal ends of the opposing arms is from about 2.5 cm to about 5 cm, preferably from about 3 cm to about 4 cm.

As more clearly shown in FIGS. 11A and 11B, the hinge 30 spaces the distal end of the arms 14 just to each side of the body. Generally, the spacing is such that the hinge flange 33 positions the arm from about 1 mm to about 8 mm, preferably from about 3 mm to about 5 mm, from the closest point of contact with the body. The use of a hinge flange avoids the additional stresses inherent in a curved hinge element as it allows a linear line of contact between the distal end of the arm and the hinge. Although certainly acceptable, those skilled in the art will recognize that an embodiment wherein the distal ends of the arms are directly connected to the circumference of the body necessitates a curvature in the line of contact which creates additional stress at that hinge point. Thus, a hinge 30 with hinge flange 33 which spaces the arms 14 from the body is preferred.

Each arm has associated therewith a press plate 20 extending away from the inner surface of the arm towards one another. As depicted in FIGS. 1, 1A and 1B, the press plates 20 are preferably comprised of a press band 24 and a press panel 22; though it is to be appreciated that either alone could suffice.

Referring to FIGS. 1A, 1B and 11A, the press band 24 has a double curved shape, the lower or distal portion of the press band defining an arc 50 having a substantially hemi-parabolic shape whose focus, if the two faces of the press band were brought into contact with each other, is at or near the proximal end 8a of the dispenser body along the longitudinal axis of the body, preferably at or slightly forward of the proximal end. The second curve of the press band is in the shape of a ramp 52 leading from the proximal point of contact of the press band, with the proximal region of the arm and meeting up with the peak of the hemi-parabola of the first curve. For lack of a better comparative, the appearance or shape of the second curve is not unlike that of a Witch of Agnesi curve, with a greater slope at its proximal end and a shallow to almost no slope at the point of contact with the parabolic curve, or of an ogee curve, with a greater arc at its proximal end and a gentler arc at the point of contact with the parabolic curve. The fundamental objective of the shape of this second curve is to provide a gradual, rolling or advancing pressure to the container body 32 as the arms are pressed towards one another.

The point at which the two curves of the press band meet defines a tappet or tappet region 16 which makes the initial contact and initial pressure point with the outer wall of the container 32. In the case of a double chambered container, the tappet causes the crushing or fracture of the dividing wall or ampoule, as appropriate. The tappet is sufficiently forward of the proximal end 8a of the body so that the structural rigidity imposed on the container body 32 by the walls 15 of the barrel 10 is no longer present. Accordingly, following upon the above discussion of the parabolic curve 50, the focus of the parabolic curve is positioned such that the tappet is properly positioned to effectively crush the dividing wall or the ampoule, as appropriate. In general, especially for a container having an internal ampoule 34, the tappet will be located from about 0.5 cm to about 1.5 cm, preferably about 1 cm, forward of the proximal end 8a of the body.

The second element of the press plates 20 as depicted in FIGS. 1, 1A, 1B, and 4, is a generally planar press panel 22 which extends from the longitudinal midline 44 of the arm 14 to the longitudinal midline 46 of the press band 24 and is contiguous with both around its full perimeter. Although depicted as a solid panel, the panel need not be solid and could have openings there through to save on materials. If such openings are present, they are preferably arranged so as not to introduce any weakness in the panel, particularly along its transverse axis, i.e., in the direction from the arm to the press band. Generally, the press panel is perhaps from about 0.5 mm to about 2 mm, preferably from about 0.5 to about 1 mm in thickness.

Furthermore, those skilled in the art will readily recognize that the press panel 22 is not needed if the press band has sufficient rigidity to prevent it from collapsing as one presses the arms towards one another. Similarly, the press band 24 need not be present so long as its thickness is sufficient to prevent its deformation upon impacting with the container wall or if there are structurally supporting ribs (not shown) integrated into the press panel to avoid such deformation. In the absence of the press band 24, the thickness of the press plates would be slightly thicker than if the press band is present: again for the purpose of ensuring its rigidity when impacting upon the container wall. Perhaps the thickness of the press panel in these instances would be on the order of from about 1 to about 3 mm in thickness. In any event, again, it is preferred that the both the press panel and the press band are present for improved performance and reinforcement in relation to the press plate overall.

To aid in securely gripping the arms of the tongs, the outer surface thereof is textured or otherwise altered to avoid slipping. For example, the outer surface may have a plurality of projections or ridges 26 extending from the surface and/or recesses extending into the surface of the arms. Alternatively, the surface may be roughened or have a rugose texture again to provide a no-slip surface. Further, the arms may be coated with a non-slip coating material, e.g., a latex coating or paint. While the aforementioned non-slip elements or treatments, whichever form is present, could extend along the full length of the outer surface of the arms, they will generally reside towards the proximal ends of arms, consistent with the most likely location a user would place their thumb and forefinger when using the dispenser handle, i.e., the touch pad area.

Finally, to further assist with the controlled dispensing of the liquid or viscous fluid, it is preferred that the distal portion of the second curve 52 of the press band in the tappet region be contoured to match the curvature of the container body. Specifically, as more clearly shown in FIGS. 1 and 4, the press band has a scalloped region 18 which mimics the curve of the container body. This provides an initial area of contact with the container rather than a point or linear point of contact. In this regard, less movement of the arms provides a greater impact upon the wall of the container. Likewise, release of the arms or a lessening of the force will have a more significant impact on releasing pressure within the container, thereby allowing backflow and/or preventing inadvertent expulsion of fluid upon initial impact, particularly in the crushing of the dividing wall or ampoule, if present.

A second embodiment of a dispenser handle is shown in FIGS. 5-8. For the most part this embodiment is the same as that presented above. Here the dispenser handle 111 has a body 116 having distal 117 and proximal 118 regions with a barrel 110 in the proximal end of the body and a tongs element 112 comprising arms 114 which flex about hinge 130, the arms 114 having inwardly projecting press plates 120 comprising a press band 124 and press panel 122 having the dual curved surface. This embodiment differs in three key aspects from that described above.

First, unlike the embodiment of FIG. 1, the face of the press band, i.e., that portion of the press band 124 that acts upon the container, does not have the scalloped press area 18 (FIG. 1). This results in an initial point of impact followed by a more linear impact upon the container than the area impact provided by the scalloped region. This may, however, help in crushing the dividing wall or ampoule, if present; especially if the dividing wall or ampoule is not readily frangible.

Figure 5:
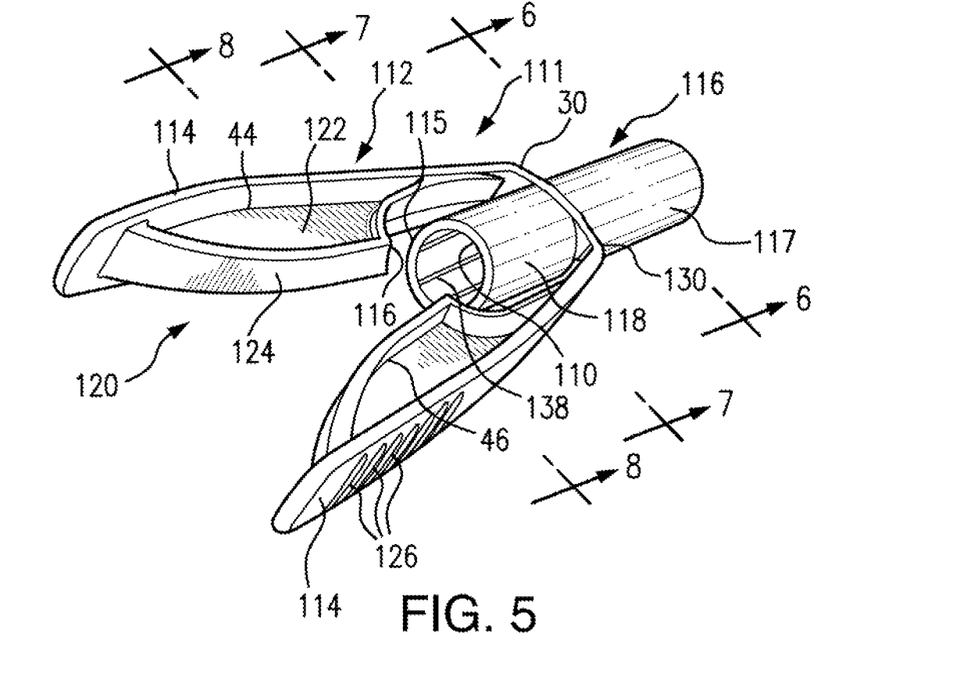
FIG. 5 is an elevated perspective view of an alternate dispenser handle constructed in accordance with the present invention.
Figure 6:
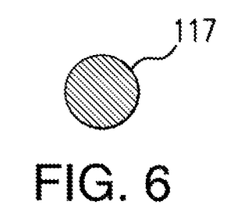
FIG. 6 is a cross-sectional view taken generally along line 6-6 of FIG. 5.

Secondly, as evident from FIGS. 5 and 6, this particular embodiment depicts a handle body whose distal portion is solid. This, however, is certainly not a preferred embodiment owing to the amount of material used. In following, the other two features as described above and below, may be, and preferably are employed with a hollow body, as described with respect to the previous embodiment.

Figure 7:
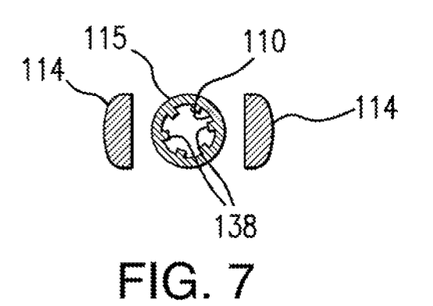
FIG. 7 is a cross-sectional view taken generally along line 7-7 of FIG. 5.
Figure 8:
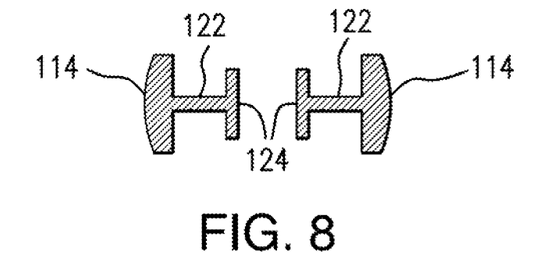
FIG. 8 is a cross-sectional view taken generally along line 8-8 of FIG. 5.

Third, this embodiment, referring to FIGS. 5 and 7, shows a preferred iteration of the barrel wherein the inner surface of the wall 115 of the barrel 110 has a plurality of projections 138 extending into the lumen of the barrel. Preferably these projections are spaced longitudinal barrel ribs or ridges or a plurality of nubs spaced, randomly or patterned, about the inner surface of the barrel wall 115. The height of the projections 138 is such as to provide a slight interference fit with the outer diameter of the container to be inserted therein. In addition to securely holding the container within the body, or assisting in that regard, the projections 138 also create an airspace between the container body and the barrel wall 115. Hence, this configuration does not present the potential for problems of trapped air or the creation of a vacuum upon inserting and removing, respectively, the container from the barrel, as may be found with the prior version, especially if the body, other than the barrel, is not hollow and/or, if hollow, does not have an open distal end. The presence of the barrel ribs allows for the easy flow of air into and out of the lower region of the barrel through the defined airspaces between the barrel wall and the container.

Figure 9:
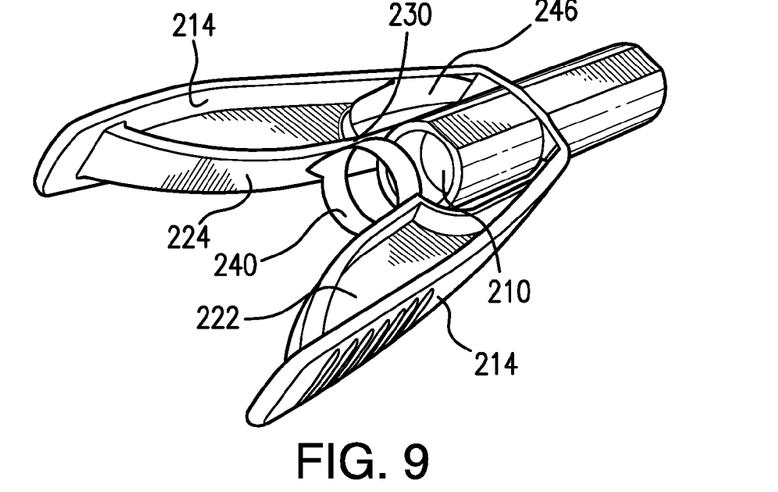
FIG. 9 is an elevated perspective partial view of a third embodiment of a dispenser handle according to the present invention.
Figure 9A:
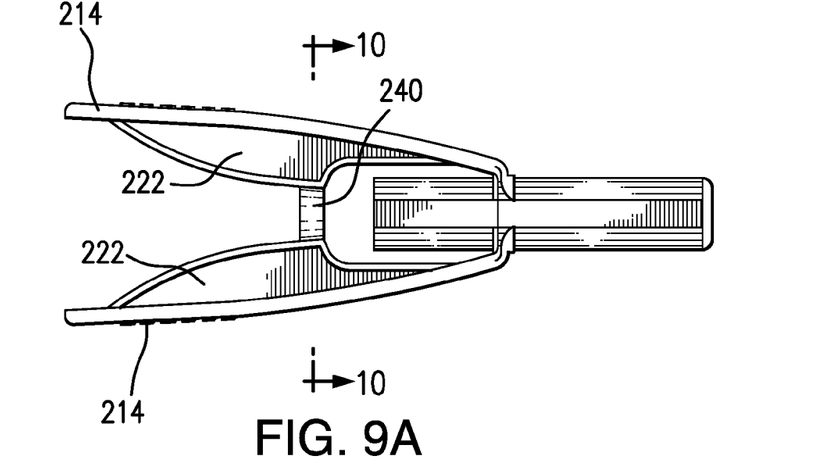
FIG. 9A is a top plan view of the dispenser handle of FIG. 9.
Figure 10:
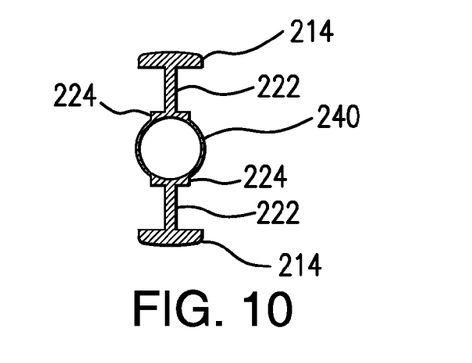
FIG. 10 is a cross-sectional view taken generally along line 10-10 of FIG. 9A.

A third embodiment of the dispenser handle is shown in FIGS. 9 and 10. This embodiment differs from the first two in relation to the presence of a tubular collar element 204 connecting the two tappet regions 230 of the prior embodiments. Here, like elements are characterized as the 2xx, wherein the xx is the numerical designation of the same elements in FIG. 1. As indicated more clearly in FIG. 10, the collar 240 is integrated into the tongs, being directly connected to the outer surface of the press bands 224, becoming a third element of the press plates. The collar 240 serves two purposes. First it helps securely hold the container in the dispenser handle as the inner diameter of the collar is preferably the same as or about the same as the outer diameter of the container to be inserted there through. Secondly, whereas in the preceding embodiments the tappet or tappet region and that portion of the press band corresponding to the second curve represents the point or area of impact of the press plate on the container, in this embodiment it is the inner wall of the collar at the point of integration or attachment with the press band 224 which acts directly upon the container outer wall. Here, the pressure to be applied to the container is actually applied by the inner wall of the collar, the forces being transferred from the press band 224 to the collar 240. Further, as shown in FIG. 9, the interior wall of the collar 240 as well as the face of the press band 224 may be contoured, as in the first embodiment discussed above, with a scalloped face which provides an initial area of contact with the container rather than an initial point or line of contact.

In use, the tubular collar will tend to change shape into a more elliptical cross-sectional shape upon pressing the arms 214 towards one another. The presence of the tubular collar provides an ever greater press area of contact between the press plate, of which it forms a part, and the outer wall of the container. This configuration is best employed with those containers that do not have a dual chamber, especially those not having an inner ampoule. The latter requires a more intense and focused impact for purposes of crushing the dividing wall or ampoule, whereas, the scalloped contour provides a more area contact. Consequently, one would likely have to apply greater pressure or force to the arms of the tongs to effect ampoule crushing with the presence of the collar than without it. Specifically, because of the area of impact associated with the scalloped region, one inherently impacts a greater surface of the container. Thus, even though one compresses the arms of both devices to the same extent to crush the ampoule, a larger surface area is being compressed in this embodiment and hence, more force or work is necessary.

Having described the dispenser handle in terms of the three embodiments above, attention is now turned to the more general aspects thereof. For example, as noted above, while the foregoing discussion has described the handle and the container to be placed therein in terms of a tubular or cylindrical shape with a circular cross section, the body of the dispenser handle and the of the container may be of alternate shapes. For example, as noted above, they may be elliptical, ovoid, rectangular, square, hexagonal, etc. provided that the shape lumen of the barrel and, if present, the collar will mimic the shape of the container to be inserted therein. Other modifications may be necessary to the press plates to accommodate the alternate shape, but those having ordinary skill in the art will readily appreciate the needed alterations in light of the present teachings.

In the preferred embodiment, as evident from FIG. 1B, the dispenser handle is a unitary piece having been formed in a single molding operation. However, it is to be understood and appreciated that the dispenser handle may comprise multiple elements. For example, it may be a two piece device wherein the tongs and the body are individually molded and then brought together. In this instance, the flange portion of the hinge element of the tongs will be accentuated, particularly in the transverse axis, whereby the flange has a central bore through it and through which the handle body passes until it reaches a point where the two are to be connected. Connection may be achieved by an electronic welding operation, bonding, or there may be press fit/interference fit elements in the outer perimeter of the handle body at the point of attachment whereby as one slides the tongs onto the dispenser body the inner circumference of the bore in the hinge flange encounters an interference fit which securely holds or engages the flange element to the dispenser body. Alternatively, the outer circumference of the dispenser body may have an annular recessed ring about the circumference of the dispenser body into which the inner circumference of the hinge flange snaps into place. Here, the diameter of the recessed ring is the same as or slightly large than the diameter of the bore such that the walls of the recess present an even greater interference fit so that when the tongs are forced past the walls, it snaps into place in the recess.

The dispenser handle is preferably made of the same material or if made in two or more parts, in similar materials selected for their intended operation. Generally speaking the composition to be used in their manufacture is one that is sufficiently stiff as to allow the dispenser handle to effect its purpose, i.e., compression of the container and, if present, crushing of the dividing wall or ampoule, while still having sufficient flexibility and resiliency that the arms may be moved inward towards each other without breaking, particularly at the hinge, and which have sufficient memory whereby when the pressure on the arms is released, the arms return to their original, or near original positions. Suitable materials include, polyolefins such as polyethylene, high density polyethylene, low density polyethylene, linear low density polyethylene, UHMWPE; halogenated polyolefins including the fluorinated versions of the foregoing; polyesters such as polyethylene terephthalate; polyamides; and compatible blends, copolymers and alloys thereof. Especially preferred, particularly in light of their low costs are the polyolefins, most especially polyethylene and polypropylene.

The dispenser handles of the present specification may be used in combination with containers of various liquids and viscous fluids and compositions. They may be used in dispensing adhesives, medicaments, cleansers, cosmetics, reagents, etc.: any application where manual application or dispensing of a liquid or viscous fluid with precision in locus and amount is needed.

The containers to be used in combination with the dispenser handles are well known and are typically used without a handle: though some devices integrate certain handle-like elements into the containers directly. Most preferably, the present dispenser handles are used with unit dose or unit application containers, i.e., those containing an amount of material for a single use or application. Exemplary containers are those disclosed in, e.g., D'Alessio et. al—U.S. Pat. Nos. 6,610,019, 6,595,940, U.S. Pat. No. 6,478,191, U.S. Pat. No. 6,340,097; Bobo et. al.—U.S. Pat. No. 6,428,234 and US 2003/0039781A1; Clark et. al.—U.S. Pat. No. 6,592,281; Badejo et. al.—US 2005/0147457A1; Voiers et. al.—U.S. Pat. No. 6,425,704 as well as in my co-filed patent application entitled Improved Container, all of which are hereby incorporated herein by reference in their entirety.

In use, the dispenser handle with the container in place is held in one's hand with the arms of the tongs typically held between the thumb and forefinger and the distal end of the dispenser body lying on the webbing of the thenar space. The arms are squeezed to release the desired liquid contained therein for application to a surface. The movement of the arms is transferred by the press plate to the container to deform the container inwardly and exert discrete localized fracturing forces against the dividing Wall or ampoule, if present. The arms provide a lever action that gains mechanical advantage as the members are squeezed toward one another. Accordingly, if the user has limited gripping strength, or if the wall of the container or, if present, the dividing wall or ampoule is exceptionally thick; the arms ensure sufficient movement to effect dispensing and, if applicable, fracturing of the dividing wall or ampoule.

Constructed and operated as previously described, this invention provides a hand-held, manually operated dispenser housing adapted to receive containers of various liquids and viscous fluids for dispensing. The manufacture is simple and comparatively inexpensive. Furthermore, it is to be appreciated that the dispenser housing is reusable as the container can simply be removed when spent and a new container inserted in its place. Of course, nothing prohibits its use as a one-time, disposable dispenser housing wherein the container is affixed into the barrel of the dispenser body, e.g., by an adhesive material. Indeed, such use may be preferable, particularly in a surgical or medical arena where reuse would require sterilization whereas the assemble device, including the container could be sterilized in a single sterilization process with the two assembled and packaged in a sealed kit or package.

While the present invention has been described with respect to aforementioned specific embodiments and examples, it should be appreciated that other embodiments utilizing the concept of the present invention are possible without departing from the scope of the invention. In this regard, since many possible embodiments may be made of the invention without departing from the scope thereof, it is to be understood that all matter herein set forth or shown in the accompanying drawings is to be interpreted as illustrative and not in a limiting sense. Similarly, it is to be appreciated that certain features and combinations and subcombinations thereof are of utility and may be employed without reference to other features and subcombinations. Finally, the present invention is further defined by the claimed elements and any and all modifications, variations, or equivalents that fall within the spirit and scope of the underlying principles embraced or embodied thereby.

We claim:

1. A dispenser handle adapted to receive a primary container of a liquid or viscous fluid composition, the dispenser handle comprising:
   (a) an elongated body having a distal end and a proximal end, the proximal end defining a barrel that is adapted to receive an end of the primary container and create an interference fit with the primary container, and a mid-section intermediate said distal and proximal ends, and a longitudinal axis running the length of the body, end to end, and
   (b) a tongs or tongs-like structure associated with and attached to or integrated into the body, comprising a pair of arms, each on opposite sides of the body, extending away from the body towards and past the proximal end of the body and angled relative to the axis of the body, said arms capable of reciprocating or flexural motion towards and away from each other, said motion being generally perpendicular to the axis of the body, wherein the opposing surfaces of the arms have contoured superstructures associated therewith and extending towards each other, but spaced from each other so that the primary container, when present, may reside in the proximal end of the body and, with or without an interference fit, between the arms, the contour of the superstructures being such that as one moves the arms towards one another, the superstructures will engage and impact upon the primary container, when present, without interference from the proximal end of the body.

2. The dispenser handle of claim 1 wherein the tongs or tongs-like structure extends from the proximal end or the mid-section of the body, and the overall dispenser handle is adapted to allow a user to hold the dispenser in one hand with the thumb and fore-finger on opposing arms and the distal end of the body lying on or near the webbing of the thenar space.

3. The dispenser of claim 2 wherein the tongs or tongs-like structure extends from the mid-section of the body.

4. The dispenser handle of claim 1 wherein the arms are at an angle of from about 15° to about 30° relative to the longitudinal axis of the body.

5. The dispenser handle of claim 1 wherein superstructures have opposing surfaces each contoured or having a portion thereof contoured to the outer surface of the primary container to be employed with the dispenser.

6. The dispenser handle of claim 1 wherein superstructures have opposing surfaces each having a distinct protrusion or tappet element at a point past the proximal end of the body.

7. The dispenser handle of claim 6 wherein superstructures also have a portion thereof contoured to the outer surface of the primary container to be employed with the dispenser.

8. The dispenser handle of claim 1 wherein the body has a passageway which allows for the egress or ingress of air as the primary container is inserted into and retracted from the barrel.

9. The dispenser handle of claim 1 wherein the barrel is defined by a plurality of ribs within the body of the dispenser which ribs create an interference fit with the primary container.

10. The dispenser handle of claim 1 wherein the tongs or tongs-like structure extends from the body at or distal of the distal end of the barrel.

11. The dispenser handle of claim 1 wherein the body is from about 4 to about 8 cm in length and the arms are from about 4 to about 8 cm in length.

12. The dispenser handle of claim 1 wherein the proximal ends of the arms are from about 2.5 cm to about 5 cm apart at rest.

13. The dispenser of claim 1 wherein each superstructure comprises a press plate having a press hand, a press panel or both.

14. The dispenser of claim 1 wherein the tongs or tongs-like structure comprises a hinge element, connecting each arm to the body, about which the arms flex.

15. A dispenser handle adapted to receive a primary container of a liquid or viscous fluid composition, the dispenser handle comprising:
(a) an elongated body having a distal end and a proximal end, the proximal end adapted to receive the primary container, and a mid-section intermediate said distal and proximal ends, and a longitudinal axis running the length of the body, end to end, and
(b) a tongs or tongs-like structure associated with and attached to or integrated into the body, comprising a pair of arms, each on opposite sides of the body, extending away from the body towards and past the proximal end of the body and angled relative to the axis of the body, said arms capable of reciprocating or flexural motion towards and away from each other, said motion being generally perpendicular to the axis of the body, wherein the opposing surfaces of the arms have contoured superstructures associated therewith and extending towards each other, but spaced from each other so that the primary container, when present, may reside in the proximal end of the body and, with or without an interference fit, between the arms, the contour of the superstructures being such that as one moves the arms towards one another, the superstructures will engage and impact upon the primary container, when present, without interference from the proximal end of the body; wherein the tongs or tongs-like structure further comprises a collar connected to or associated with the opposing surfaces of the superstructure, which collar defines a space through which the primary container, when situated in the proximal end of the body, will extend.

16. The dispenser handle of claim 15 wherein the tongs or tongs-like structure extends from the proximal end or the mid-section of the body, and the overall dispenser handle is adapted to allow a user to hold the dispenser in one hand with the thumb and fore-finger on opposing arms and the distal end of the body lying on or near the webbing of the thenar space.

17. The dispenser handle of claim 15 wherein the arms are at an angle of from about 15° to about 30° relative to the longitudinal axis of the body.

18. The dispenser handle of claim 15 wherein superstructures have opposing surfaces each contoured or having a portion thereof contoured to the outer surface of the primary container to be employed with the dispenser.

19. The dispenser handle of claim 15 wherein the body is from about 4 to about 8 cm in length and the arms are from about 4 to about 8 cm in length.

20. The dispenser handle of claim 15 wherein the proximal ends of the arms are from about 2.5 cm to about 5 cm apart at rest.

* * * * *